(12) United States Patent
Connor et al.

(10) Patent No.: US 8,721,566 B2
(45) Date of Patent: May 13, 2014

(54) SPINAL MOTION MEASUREMENT DEVICE

(76) Inventors: Robert A. Connor, Minneapolis, MN (US); Hart Garner, Minneapolis, MN (US)

( * ) Notice: Subject to any disclaimer, the term of this patent is extended or adjusted under 35 U.S.C. 154(b) by 382 days.

(21) Appl. No.: 12/927,348

(22) Filed: Nov. 12, 2010

(65) Prior Publication Data

US 2012/0123301 A1    May 17, 2012

(51) Int. Cl.
| | |
|---|---|
| *A61B 5/103* | (2006.01) |
| *A61B 5/117* | (2006.01) |
| *A61B 17/56* | (2006.01) |
| *A61F 5/04* | (2006.01) |
| *A61B 17/00* | (2006.01) |
| *A61F 4/00* | (2006.01) |
| *A61B 17/70* | (2006.01) |
| *A61B 17/88* | (2006.01) |

(52) U.S. Cl.
USPC ............. 600/587; 600/594; 600/595; 606/53; 606/54; 606/57; 606/251; 606/252; 606/279; 606/257; 606/246; 606/258; 623/23.47

(58) Field of Classification Search
USPC ........ 600/587, 594, 595; 606/53, 54, 57, 251, 606/252, 279, 257, 246, 258; 623/23.47
See application file for complete search history.

(56) References Cited

U.S. PATENT DOCUMENTS

| | | | | |
|---|---|---|---|---|
| 2,180,775 | A * | 11/1939 | Stevens | 606/237 |
| 3,865,105 | A * | 2/1975 | Lode | 606/54 |
| 4,699,156 | A * | 10/1987 | Gracovetsky | 600/594 |
| 4,872,268 | A * | 10/1989 | Perrault | 33/512 |
| 4,899,761 | A * | 2/1990 | Brown et al. | 600/594 |
| 4,932,975 | A | 6/1990 | Main et al. | |
| 4,971,069 | A * | 11/1990 | Gracovetsky | 600/594 |
| 4,988,349 | A * | 1/1991 | Pennig | 606/58 |
| 5,059,194 | A * | 10/1991 | Michelson | 606/90 |
| 5,092,866 | A | 3/1992 | Breard et al. | |
| 5,101,835 | A * | 4/1992 | DelRe | 600/594 |
| 5,107,839 | A | 4/1992 | Houdek et al. | |
| 5,145,661 | A * | 9/1992 | Schneider et al. | 424/9.322 |
| 5,146,929 | A * | 9/1992 | Sawhill | 600/594 |
| 5,213,112 | A | 5/1993 | Niwa et al. | |
| 5,219,349 | A * | 6/1993 | Krag et al. | 606/53 |
| 5,291,901 | A * | 3/1994 | Graf | 600/594 |
| 5,329,933 | A * | 7/1994 | Graf | 600/594 |
| 5,334,203 | A * | 8/1994 | Wagner | 606/252 |
| 5,337,758 | A * | 8/1994 | Moore et al. | 600/594 |
| 5,375,823 | A | 12/1994 | Navas | |
| 5,398,697 | A * | 3/1995 | Spielman | 600/594 |
| 5,400,800 | A * | 3/1995 | Jain et al. | 600/595 |
| 5,415,661 | A | 5/1995 | Holmes | |

(Continued)

*Primary Examiner* — Rene Towa
*Assistant Examiner* — May Abouelela

(57) ABSTRACT

This invention is a minimally-invasive device, including bone-moving members and motion-measuring members, that can help surgeons to obtain objective, quantitative information concerning spinal flexion, extension, lateral bending, decompression, compression and torsion in order to select the best therapy for each patient. The prior art does not offer surgeons the opportunity to objectively and independently measure each of these movements. As a result, currently there is tremendous variation concerning which therapies are selected for which conditions. It is very unlikely that quality is being optimized and costs are being best managed with such high variation in practice patterns. This variation may be greatly reduced by the availability of objective information concerning spinal motion from this device. In this manner, this device can help surgeons to select the optimal therapy, to improve the quality of care, and to reduce the risk and expense of unnecessary spinal procedures and hardware.

7 Claims, 7 Drawing Sheets

(56) References Cited

U.S. PATENT DOCUMENTS

| | | | |
|---|---|---|---|
| 5,471,995 A | 12/1995 | Halliday | |
| 5,474,086 A * | 12/1995 | McCormick et al. | 600/595 |
| 5,480,401 A | 1/1996 | Navas | |
| 5,501,684 A | 3/1996 | Schlapfer et al. | |
| 5,540,688 A | 7/1996 | Navas | |
| 5,582,189 A | 12/1996 | Pannozzo | |
| 5,626,579 A | 5/1997 | Muschler et al. | |
| 5,640,971 A * | 6/1997 | Martin, Jr. | 600/594 |
| 5,647,375 A * | 7/1997 | Farfan de los Godos | 600/594 |
| 5,658,286 A * | 8/1997 | Sava | 606/279 |
| 5,662,122 A | 9/1997 | Evans | |
| 5,672,175 A | 9/1997 | Martin | |
| 5,688,280 A | 11/1997 | Booth et al. | |
| 5,704,939 A | 1/1998 | Justin | |
| 5,772,610 A * | 6/1998 | McGorry et al. | 600/594 |
| 5,819,428 A | 10/1998 | Meyer | |
| RE36,221 E * | 6/1999 | Breard et al. | 606/54 |
| 5,944,664 A | 8/1999 | Hayashi | |
| 5,951,556 A * | 9/1999 | Faccioli et al. | 606/65 |
| 5,966,827 A * | 10/1999 | Horvath et al. | 33/512 |
| 6,001,130 A | 12/1999 | Bryan et al. | |
| 6,033,412 A | 3/2000 | Losken et al. | |
| 6,106,525 A | 8/2000 | Sachse | |
| 6,205,411 B1 | 3/2001 | DiGioia et al. | |
| 6,245,075 B1 | 6/2001 | Betz et al. | |
| 6,290,700 B1 | 9/2001 | Schmotzer | |
| 6,296,643 B1 | 10/2001 | Hopf et al. | |
| 6,299,613 B1 | 10/2001 | Ogilvie et al. | |
| 6,332,887 B1 * | 12/2001 | Knox | 606/87 |
| 6,340,363 B1 | 1/2002 | Bolger et al. | |
| 6,375,682 B1 | 4/2002 | Fleischmann et al. | |
| 6,417,750 B1 | 7/2002 | Sohn | |
| 6,425,920 B1 | 7/2002 | Hamada | |
| 6,434,415 B1 | 8/2002 | Foley et al. | |
| 6,470,207 B1 | 10/2002 | Simon et al. | |
| 6,474,341 B1 | 11/2002 | Hunter et al. | |
| 6,475,220 B1 | 11/2002 | Whiteside | |
| 6,499,488 B1 | 12/2002 | Hunter et al. | |
| 6,500,131 B2 | 12/2002 | Leitner et al. | |
| 6,539,328 B1 | 3/2003 | Cremonese et al. | |
| 6,616,669 B2 | 9/2003 | Ogilvie et al. | |
| 6,656,135 B2 * | 12/2003 | Zogbi et al. | 600/594 |
| 6,673,079 B1 | 1/2004 | Kane | |
| 6,682,533 B1 | 1/2004 | Dinsdale et al. | |
| 6,706,005 B2 | 3/2004 | Roy et al. | |
| 6,709,433 B1 * | 3/2004 | Schoenefeld | 606/57 |
| 6,716,216 B1 | 4/2004 | Boucher et al. | |
| 6,835,207 B2 | 12/2004 | Zacouto et al. | |
| 6,849,076 B2 | 2/2005 | Blunn et al. | |
| 6,875,211 B2 * | 4/2005 | Nichols et al. | 606/914 |
| 6,918,910 B2 | 7/2005 | Smith et al. | |
| 6,969,360 B1 | 11/2005 | Pai et al. | |
| 6,986,771 B2 | 1/2006 | Paul et al. | |
| 6,989,011 B2 | 1/2006 | Paul et al. | |
| 7,011,658 B2 * | 3/2006 | Young | 606/258 |
| 7,014,617 B2 | 3/2006 | Grinberg | |
| 7,066,957 B2 | 6/2006 | Graf | |
| 7,083,621 B2 | 8/2006 | Shaolian et al. | |
| 7,107,091 B2 | 9/2006 | Jutras et al. | |
| 7,125,410 B2 | 10/2006 | Freudiger | |
| 7,131,952 B1 * | 11/2006 | Dickholtz et al. | 600/594 |
| 7,135,022 B2 | 11/2006 | Kosashvili et al. | |
| 7,153,281 B2 | 12/2006 | Holmes | |
| 7,172,561 B2 | 2/2007 | Grinberg | |
| 7,182,736 B2 | 2/2007 | Roy et al. | |
| 7,229,441 B2 | 6/2007 | Trieu et al. | |
| 7,291,150 B2 * | 11/2007 | Graf | 606/86 A |
| 7,326,210 B2 | 2/2008 | Jahng et al. | |
| 7,329,258 B2 | 2/2008 | Studer | |
| 7,351,244 B2 | 4/2008 | Hamada | |
| 7,361,196 B2 | 4/2008 | Fallin et al. | |
| 7,481,841 B2 | 1/2009 | Hazebrouck et al. | |
| 7,491,179 B2 | 2/2009 | Roy et al. | |
| 7,507,242 B2 * | 3/2009 | Triplett et al. | 606/87 |
| 7,559,951 B2 | 7/2009 | DiSilvestro et al. | |
| 7,611,526 B2 | 11/2009 | Carl et al. | |
| 7,658,753 B2 | 2/2010 | Carl et al. | |
| 7,691,130 B2 | 4/2010 | Bruneau et al. | |
| 7,708,737 B2 | 5/2010 | Kraft et al. | |
| 7,708,765 B2 * | 5/2010 | Carl et al. | 606/279 |
| 7,708,779 B2 | 5/2010 | Edie et al. | |
| 7,722,675 B2 | 5/2010 | Ralph et al. | |
| 7,736,305 B2 | 6/2010 | DiPoto | |
| 7,763,053 B2 | 7/2010 | Gordon | |
| 7,766,941 B2 | 8/2010 | Paul | |
| 7,776,051 B2 * | 8/2010 | Colleran et al. | 606/105 |
| 7,931,651 B2 * | 4/2011 | Webb et al. | 606/59 |
| 7,993,269 B2 * | 8/2011 | Donofrio et al. | 600/309 |
| 8,092,495 B2 * | 1/2012 | Boulis et al. | 606/246 |
| 8,162,979 B2 * | 4/2012 | Sachs et al. | 606/246 |
| 8,182,483 B2 * | 5/2012 | Bagnasco et al. | 606/58 |
| 8,211,149 B2 * | 7/2012 | Justis | 606/258 |
| 8,241,231 B2 * | 8/2012 | Bausewein et al. | 600/594 |
| 8,357,184 B2 * | 1/2013 | Woolley et al. | 606/279 |
| 8,366,710 B2 * | 2/2013 | Hirata et al. | 606/57 |
| 8,377,099 B1 * | 2/2013 | Stauber | 606/261 |
| 8,435,269 B2 * | 5/2013 | Woolley et al. | 606/279 |
| 8,506,599 B2 * | 8/2013 | Jackson | 606/264 |
| 8,523,865 B2 * | 9/2013 | Reglos et al. | 606/79 |
| 2002/0143330 A1 * | 10/2002 | Shluzas | 606/61 |
| 2002/0151978 A1 | 10/2002 | Zacouto et al. | |
| 2003/0038196 A1 | 2/2003 | Moriya et al. | |
| 2003/0220590 A1 | 11/2003 | Csonka | |
| 2004/0049190 A1 | 3/2004 | Biedermann et al. | |
| 2004/0059261 A1 | 3/2004 | Grinberg | |
| 2004/0059262 A1 | 3/2004 | Grinberg | |
| 2004/0116835 A1 | 6/2004 | Holmes | |
| 2004/0122427 A1 | 6/2004 | Holmes | |
| 2004/0143264 A1 | 7/2004 | McAfee | |
| 2004/0152972 A1 | 8/2004 | Hunter | |
| 2004/0167520 A1 | 8/2004 | Zucherman et al. | |
| 2004/0215191 A1 | 10/2004 | Kitchen | |
| 2004/0236424 A1 | 11/2004 | Berez et al. | |
| 2004/0267279 A1 * | 12/2004 | Casutt et al. | 606/104 |
| 2005/0021040 A1 * | 1/2005 | Bertagnoli | 606/90 |
| 2005/0043621 A1 | 2/2005 | Perlin | |
| 2005/0055025 A1 | 3/2005 | Zacouto et al. | |
| 2005/0065516 A1 | 3/2005 | Jahng | |
| 2005/0070917 A1 * | 3/2005 | Justis | 606/104 |
| 2005/0085814 A1 | 4/2005 | Sherman | |
| 2005/0124991 A1 | 6/2005 | Jahng | |
| 2005/0149020 A1 | 7/2005 | Jahng | |
| 2005/0154390 A1 | 7/2005 | Biedermann et al. | |
| 2005/0171543 A1 | 8/2005 | Timm et al. | |
| 2005/0177156 A1 | 8/2005 | Timm et al. | |
| 2005/0177239 A1 * | 8/2005 | Steinberg | 623/17.12 |
| 2005/0192569 A1 * | 9/2005 | Nichols et al. | 606/53 |
| 2005/0203514 A1 * | 9/2005 | Jahng et al. | 606/61 |
| 2005/0234555 A1 | 10/2005 | Sutton et al. | |
| 2005/0245929 A1 | 11/2005 | Winslow et al. | |
| 2005/0288672 A1 | 12/2005 | Ferree | |
| 2006/0004447 A1 | 1/2006 | Mastrorio et al. | |
| 2006/0036246 A1 | 2/2006 | Carl et al. | |
| 2006/0036256 A1 | 2/2006 | Carl et al. | |
| 2006/0036259 A1 | 2/2006 | Carl et al. | |
| 2006/0036324 A1 | 2/2006 | Sachs et al. | |
| 2006/0047282 A1 | 3/2006 | Gordon | |
| 2006/0084983 A1 | 4/2006 | Kim | |
| 2006/0084985 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085073 A1 | 4/2006 | Raiszadeh | |
| 2006/0085074 A1 | 4/2006 | Raiszadeh | |
| 2006/0129147 A1 | 6/2006 | Biedermann et al. | |
| 2006/0173454 A1 * | 8/2006 | Spitler et al. | 606/61 |
| 2006/0195095 A1 | 8/2006 | Mueller et al. | 606/61 |
| 2006/0212033 A1 | 9/2006 | Rothman et al. | 606/61 |
| 2006/0217712 A1 * | 9/2006 | Mueller et al. | 606/61 |
| 2006/0247637 A1 | 11/2006 | Colleran et al. | |
| 2006/0265077 A1 | 11/2006 | Zwirkoski | |
| 2007/0016193 A1 | 1/2007 | Ritland | |
| 2007/0123871 A1 | 5/2007 | Jahng | |
| 2007/0161991 A1 | 7/2007 | Altarac et al. | |

(56) References Cited

U.S. PATENT DOCUMENTS

| | | | | |
|---|---|---|---|---|
| 2007/0173832 A1 | | 7/2007 | Tebbe et al. | |
| 2007/0173855 A1* | | 7/2007 | Winn et al. | 606/90 |
| 2007/0179409 A1* | | 8/2007 | Roy et al. | 600/587 |
| 2007/0191846 A1* | | 8/2007 | Bruneau et al. | 606/61 |
| 2007/0198088 A1 | | 8/2007 | Biedermann et al. | |
| 2007/0232958 A1* | | 10/2007 | Donofrio et al. | 600/587 |
| 2007/0233065 A1 | | 10/2007 | Donofrio et al. | |
| 2007/0233075 A1 | | 10/2007 | Dawson | |
| 2007/0233098 A1 | | 10/2007 | Mastrorio et al. | |
| 2007/0233254 A1 | | 10/2007 | Grotz et al. | |
| 2007/0239159 A1* | | 10/2007 | Altarac et al. | 606/61 |
| 2007/0239161 A1 | | 10/2007 | Giger et al. | |
| 2007/0255088 A1 | | 11/2007 | Jacobson et al. | |
| 2007/0270803 A1 | | 11/2007 | Giger et al. | |
| 2007/0270821 A1 | | 11/2007 | Trieu et al. | |
| 2007/0270860 A1 | | 11/2007 | Jackson | |
| 2007/0276369 A1 | | 11/2007 | Allard et al. | |
| 2007/0282443 A1 | | 12/2007 | Globerman et al. | |
| 2007/0288011 A1* | | 12/2007 | Logan | 606/61 |
| 2007/0293862 A1 | | 12/2007 | Jackson | |
| 2008/0021466 A1 | | 1/2008 | Shadduck et al. | |
| 2008/0045951 A1 | | 2/2008 | Fanger et al. | |
| 2008/0097441 A1 | | 4/2008 | Hayes et al. | |
| 2008/0114357 A1 | | 5/2008 | Allard et al. | |
| 2008/0125777 A1* | | 5/2008 | Veldman et al. | 606/61 |
| 2008/0154307 A1* | | 6/2008 | Colleran et al. | 606/257 |
| 2008/0161933 A1 | | 7/2008 | Grotz et al. | |
| 2008/0177317 A1 | | 7/2008 | Jackson | |
| 2008/0177388 A1 | | 7/2008 | Patterson et al. | |
| 2008/0208080 A1* | | 8/2008 | Ichikawa et al. | 600/594 |
| 2008/0221620 A1 | | 9/2008 | Krause | |
| 2008/0255575 A1* | | 10/2008 | Justis et al. | 606/102 |
| 2008/0269904 A1 | | 10/2008 | Voorhies | |
| 2008/0288073 A1 | | 11/2008 | Renganath et al. | |
| 2008/0306553 A1* | | 12/2008 | Zucherman et al. | 606/301 |
| 2008/0312693 A1 | | 12/2008 | Trautwein et al. | |
| 2008/0319351 A1* | | 12/2008 | Chow et al. | 600/594 |
| 2008/0319486 A1 | | 12/2008 | Hestad et al. | |
| 2009/0005709 A1* | | 1/2009 | Gagne | 600/594 |
| 2009/0012562 A1 | | 1/2009 | Hestad et al. | |
| 2009/0012565 A1* | | 1/2009 | Sachs et al. | 606/246 |
| 2009/0076597 A1 | | 3/2009 | Dahlgren et al. | |
| 2009/0093820 A1* | | 4/2009 | Trieu et al. | 606/103 |
| 2009/0112207 A1 | | 4/2009 | Walker et al. | |
| 2009/0112262 A1 | | 4/2009 | Pool et al. | |
| 2009/0112263 A1 | | 4/2009 | Pool et al. | |
| 2009/0234250 A1* | | 9/2009 | Bausewein et al. | 600/594 |
| 2009/0234388 A1 | | 9/2009 | Patterson et al. | |
| 2009/0234456 A1 | | 9/2009 | Nycz | |
| 2009/0264796 A1* | | 10/2009 | Pope et al. | 600/594 |
| 2009/0281542 A1* | | 11/2009 | Justis | 606/60 |
| 2010/0030184 A1* | | 2/2010 | Boulis et al. | 604/500 |
| 2010/0049204 A1 | | 2/2010 | Soubeiran | |
| 2010/0070033 A1 | | 3/2010 | Doty | |
| 2010/0094302 A1 | | 4/2010 | Pool | |
| 2010/0094303 A1 | | 4/2010 | Chang et al. | |
| 2010/0094304 A1 | | 4/2010 | Pool | |
| 2010/0094305 A1 | | 4/2010 | Chang | |
| 2010/0094306 A1 | | 4/2010 | Chang | |
| 2010/0100133 A1 | | 4/2010 | Carl et al. | |
| 2010/0114103 A1 | | 5/2010 | Harrison et al. | |
| 2010/0145387 A1 | | 6/2010 | Bruneau et al. | 606/249 |
| 2010/0191288 A1 | | 7/2010 | Carl et al. | |
| 2010/0198226 A1* | | 8/2010 | Estes et al. | 606/90 |
| 2010/0198261 A1 | | 8/2010 | Trieu et al. | |
| 2010/0262160 A1 | | 10/2010 | Boyden et al. | |
| 2010/0262239 A1 | | 10/2010 | Boyden et al. | |
| 2010/0262247 A1 | | 10/2010 | Arnin | |
| 2010/0268119 A1* | | 10/2010 | Morrison | 600/587 |
| 2011/0092859 A1* | | 4/2011 | Neubardt | 600/594 |
| 2011/0172566 A1* | | 7/2011 | Kawchuk | 600/587 |
| 2011/0295159 A1* | | 12/2011 | Shachar et al. | 600/594 |
| 2011/0313323 A1* | | 12/2011 | Henderson et al. | 600/594 |
| 2012/0179070 A1* | | 7/2012 | Pommer et al. | 600/594 |
| 2012/0203282 A1* | | 8/2012 | Sachs et al. | 606/278 |
| 2012/0232429 A1* | | 9/2012 | Fischer et al. | 600/592 |

* cited by examiner

SPINAL MOTION MEASUREMENT DEVICE

CROSS-REFERENCE TO RELATED APPLICATIONS

Not Applicable

FEDERALLY SPONSORED RESEARCH

Not Applicable

SEQUENCE LISTING OR PROGRAM

Not Applicable

FIELD OF INVENTION

This invention relates to devices for measuring skeletal motion.

INTRODUCTION AND REVIEW OF THE PRIOR ART

Chronic lower back pain is a very common, significant, and costly health problem in the United States and the entire world. It is estimated that more than ten million people in the U.S. alone suffer from chronic back pain at any a given time, that the annual prevalence of lower back pain is in the range of 15-45% of the population, and that thoracic and lumbar spinal disorders affect nearly three-quarters of the U.S. population some time during their lives. Chronic back pain can be debilitating, interfering with one's ability to work and enjoy recreational activities. It is the most common activity-limiting condition affecting people under the age of 45.

The leading cause of chronic lower back pain is the degeneration of the semi-flexible discs between spinal vertebrae. There are non-invasive approaches to address chronic back pain, but sometimes they are inadequate and more invasive methods are required. Historically, a common invasive method has been to fuse selected spinal vertebrae together in an effort to eliminate disc movement and stop the pain. More than 150,000 lumbar fusions are done each year to immobilize selected vertebrae. However, there are limitations associated with fusing vertebrae. Fusion-related limitations include: undesirable restriction of natural spine movement (flexion, extension, lateral bending, and torsion) in fused segments; greater stress and degeneration affecting spinal segments adjacent to fused segments (a phenomenon called "transition syndrome"); bone loss in the immobilized segments; failure to stop the pain in approximately 20-25% of fusion cases; irreversibility of the procedure; and the invasiveness, health risks, and relatively long recovery period associated with the surgery.

Due to the limitations associated with the complete immobilization of selected vertebrae in fusion, there has been an increasing trend toward alternative methods of addressing back pain that preserve some spinal mobility. Dynamic stabilization is the term for methods that seek to maintain desirable spinal movement, but limit undesirable spinal movement. The ultimate form of dynamic stabilization would be to artificially recreate the natural biodynamics of a healthy spine. Since the original spine is not entirely replaced, the challenge is to recreate natural biodynamics in an integrated manner with those portions of the original spine which are working properly and remain in place. Due to the complexity of spinal biomechanics, this is not an easy goal.

Dynamic stabilization can be implemented in the intervertebral space (such as with artificial discs), in the space posterior to the vertebrae (such as with flexible connecting rods), or in both places simultaneously. With respect to the intervertebral space, malfunctioning disc tissue may be replaced with an artificial alternative. With respect to the space posterior to vertebrae, selected vertebrae may be connected by an elastic cord, a cord with spacer, a flexible rod, or by some other type of connecting member that allows some movement. Both spaces may be addressed in combination to distribute loading in a manner that approximates the loading distribution in a healthy spine.

Spinal movements are often categorized into flexion, extension, lateral bending, decompression, compression, and torsion. These movements may be informally defined as follows: spinal flexion is "bending forward"; spinal extension is "bending backwards"; spinal lateral bending is "bending to the right or left"; spinal decompression is "vertical elongation"; spinal compression is "vertical shortening" of the spine; spinal torsion is "vertical twisting." However, these informal definitions are not sufficiently precise for evaluating the prior art. These informal definitions are inadequate for isolating these movements from each other. In the prior art, these individual movements are either confounded or not measured at all. For these reasons, we now present more formal and precise definitions of spinal flexion, extension, lateral bending, decompression, compression, and torsion.

Spinal flexion may be formally defined as spinal movement that changes a linear angle formed by the intersection of the lateral cross-sectional planes of two vertebrae, wherein the vertex of this angle is anterior to the center of the vertebrae. The amount of flexion is the degree of the linear angle formed by the intersection of the lateral cross-sectional planes of two vertebrae, wherein the vertex of this angle is anterior to the center of the vertebrae. Simple application of one or more forces to a single point on each of the vertebrae (either directly to the vertebrae or to members inserted into the vertebrae) does not provide sufficient control to adjust and measure flexion independently from decompression and compression.

Spinal extension may be formally defined as spinal movement that changes a linear angle formed by the intersection of the lateral cross-sectional planes of two vertebrae, wherein the vertex of this angle is posterior to the center of the vertebrae. The amount of extension is the degree of the linear angle formed by the intersection of the lateral cross-sectional planes of two vertebrae, wherein the vertex of this angle is posterior to the center of the vertebrae. Simple application of one or more forces to a single point on each of the vertebrae (either directly to the vertebrae or to members inserted into the vertebrae) does not provide sufficient control to adjust and measure extension independently from decompression and compression.

Spinal lateral bending may be formally defined as spinal movement that changes a linear angle formed by the intersection of the lateral cross-sectional planes of two vertebrae, wherein the vertex of this angle is to the right or left of the center of the vertebrae. The amount of lateral bending is the degree of the linear angle formed by the intersection of the lateral cross-sectional planes of two vertebrae, wherein the vertex of this angle is to the right or left of the center of the vertebrae. Simple application of one or more forces to a single point on each of the vertebrae (either directly to the vertebrae or to members inserted into the vertebrae) does not provide sufficient control to adjust and measure lateral bending independently from decompression and compression.

Spinal decompression may be formally defined as spinal movement that increases the average distance between all points in the lateral cross-sections of two spinal vertebrae. Simple application of one or more forces to a single point on each of the vertebrae (either directly to the vertebrae or to members inserted into the vertebrae) does not provide sufficient control to adjust and measure decompression independently from flexion, extension, and/or lateral bending.

Spinal compression may be formally defined as spinal movement that decreases the average distance between all points in the lateral cross-sections of two spinal vertebrae. Simple application of one or more forces to a single point on each of the vertebrae (either directly to the vertebrae or to members inserted into the vertebrae) does not provide sufficient control to adjust and measure compression independently from flexion, extension, and/or lateral bending.

Spinal torsion may be formally defined as spinal movement that rotates the lateral cross-sectional plane of one vertebra around the vertical axis of the vertebra relative to the cross-sectional plane of a second vertebra. Application of forces to points that are vertically aligned on vertebrae does not allow independent adjustment and measurement of torsion.

U.S. Pat. No. 4,899,761, "Apparatus and Method for Measuring Spinal Instability" (Brown and Holmes, 1990) discloses a device for measuring spinal instability. This device comprises a vertebrae distractor with a pair of distractor arms, driven by a motor, which separate the vertebrae of a motion segment unit of the spine. This device also measures the resistance of those vertebrae to this force. U.S. Patent Application 20040116835 and U.S. Pat. No. 7,153,281, "Apparatus and Method for Measuring Instability of a Motion Segment Unit of a Spine," (Holmes, 2004 and 2006) appear to build upon this concept with a device that has a distractor arm assembly with a pivotal collar assembly along a centrally positioned jackscrew. This patent discloses an apparatus with a pair of segmented arms each having at least two arm segments pivotal with respect to each other. U.S. Patent Application No. 20040122427, "Apparatus and Method for Restoring Biomechanical Function to a Motion Segment Unit of the Spine," (Holmes, 2004) discloses the use of pre and post decompression measurements of at least one characteristic of the targeted motion segment unit to identify a suitable device for correcting instability of the targeted motion segment unit.

U.S. Pat. Nos. 4,899,761 and 7,153,281 and U.S. Patent Application Nos. 200400116835 and 20040122427 are valuable and innovative advances in the field of spinal motion measurement and treatment. However, they appear to have limitations with respect to independent and complete control of flexion, extension, lateral bending, decompression, compression, and torsion. First, these patents appear to confound measurement of flexion or extension vs. compression or decompression. They do not appear to allow a user to control flexion or extension independently of decompression or compression. For example, when the distractor arm separates vertebrae, it appears to cause movement that confounds flexion and decompression. When the distractor arm compresses vertebrae, it appears to cause movement that confounds extension and compression. Second, these patents do not appear to offer the user independent control over lateral bending and torsion. Third, these patents do not appear to offer symmetric control over extension vs. flexion because of the asymmetric dynamics of compression vs. decompression of the intervertebral disc. As we will discuss, the invention disclosed in this present application addresses all three of these limitations.

U.S. Pat. No. 5,213,112, "Tension Meter for Orthopedic Surgery," (Niwa et al., 1993) discloses a tension meter for measuring the degree of tension between bones. U.S. Patent Application No. 20040059261 and U.S. Pat. No. 7,014,617, "Pivoted Tensiometer for Measuring Tension in an Intervertebral Disc Space," (Grinberg, 2004 and 2006) disclose a pivoted tensiometer adapted for use in measuring tension in an intervertebral disc space. U.S. Patent Application No. 20040059262 and U.S. Pat. No. 7,172,561, "Spreader Tensiometer for Measuring Tension in an Intervertebral Disc Space," (Grinberg, 2004 and 2007) disclose a tensiometer for measuring tension in an intervertebral disc space between opposed vertebral surfaces with a disc space spreader adapted to enter a disc space and distract the disc space upon rotation. U.S. Pat. No. 6,425,920, "Spinal Fusion Implant," (Hamada, 2002) and U.S. Pat. No. 7,351,244, "Spinal Fusion Instrumentation Implant and Method," (Hamada, 2008) disclose systems of surgical instrumentation, implants, bone graft material, and measurement equipment that enable measurement of the characteristics of the intervertebral space. These systems include devices that are inserted into, and spread within, the intervertebral space.

These five devices (Niwa et al., 1993; Grinberg, 2006; Grinberg, 2007; Hamada, 2002; and Hamada, 2008) are limited in applicability because they are relatively-invasive, appear to measure primarily decompression (or decompression confounded by flexion), and appear to only apply expanding force at a single point on each skeletal member. None of these devices offers independent control and measurement of spinal flexion, extension, lateral bending, decompression, compression, and torsion.

U.S. Pat. Nos. 6,706,005, 7,182,736, and 7491179, "Apparatus and Method for Assessing Loads on Adjacent Bones," (Roy et. al., 2004, 2007, and 2009) appear to disclose one or more devices that use MicroElectroMechanical Systems (MEMS) to provide an in vivo assessment of loads on adjacent bones. Such devices can be useful for measuring skeletal load via pressure, but do not appear useful for measuring the range of motion in flexion, extension, lateral bending, decompression, compression, or torsion of the spine as proposed in this application.

U.S. Pat. No. 6,539,328, "Device and Process for Measurement and Treatment of Spinal Mobility," (Cremones et al., 2003) appears to disclose a device for measuring spinal mobility that can determine spinal segment mobility by applying a force impulse to a spinal segment and generating a waveform characteristic of spinal mobility. U.S. Pat. No. 5,662,122, "Method and Apparatus for Objectively Assessing and Correcting the Relative Compliance of Vertebral Segments," (Evans, 1997) discloses a device and method involving application of a uniform low-energy diagnostic impulse to each vertebral segment of interest and recording the resulting force waveform. Both of these devices appear to focus on the response of the spine to force impulses. They do not appear to offer independent control and measurement of spinal flexion, extension, lateral bending, decompression, compression, and torsion. Further, these devices appear to be most applicable in open surgery that allows direct access to the bone. In minimally-invasive operations, use of direct force impact devices would likely be limited by the cushioning effect of soft tissue between the skin and the bone. In contrast, the device proposed in this application offers independent control and measurement of spinal flexion, extension, lateral bending, decompression, compression, and torsion in a minimally-invasive manner.

U.S. Pat. No. 5,101,835, "Method and Apparatus for Testing a Spine," (DelRe et al., 1992) discloses a non-invasive method for testing for dysfunctional discs in which an external roller exerts pressure on the spine and measures resulting spinal movement. U.S. Pat. No. 5,471,995, "Spine Contour Gauge and Method," (Halliday, 1995) discloses an external device for quantitatively measuring spinal contours and flexibility. This device includes a plurality of substantially parallel coplanar shafts that gently deploy against a patient's spine. Due to their external nature, these two devices appear to offer limited control over flexion and extension and virtually no control over lateral bending, decompression, compression, and torsion.

To summarize, the prior art has limitations and does not provide surgeons with the capability for minimally-invasive, independent control and objective measurement of spinal flexion, extension, lateral bending, decompression, compression, and torsion. There is an unmet clinical need for a device to provide surgeons with this capability. Such a device can guide therapeutic selection to improve the quality of care, as well as reduce the cost and risk of unnecessary procedures and hardware. The novel device that we will now disclose herein can provide this capability and meet this clinical need.

SUMMARY AND ADVANTAGES OF THIS INVENTION

This invention is a minimally-invasive device that provides surgeons with objective information on spinal flexion, extension, lateral bending, decompression, compression and torsion that can help surgeons to select the optimal therapies to correct spinal conditions. This can improve the quality of care and reduce the risk and expense of unnecessary spinal procedures and hardware. The prior art does not offer surgeons the opportunity to objectively and independently adjust and measure each of these spinal movements. This device does.

This device includes one or more bone moving members that cause movement of spinal vertebrae relative to each other. The surgeon can select this movement from one (or a combination) of the movements in the group consisting of flexion, extension, lateral bending, decompression, compression, and torsion. As an advantage over prior art in this area, this device allows a surgeon to adjust the amounts of flexion, extension, or lateral bending independently of the amount of decompression or compression. As another advantage, this device also allows a surgeon to independently test spinal torsion.

This device also includes one or more bone movement measuring members. These movement measuring members measure the movement of spinal vertebrae relative to each other as a result of the forces applied by the bone moving members. This device also includes one or more movement analyzing members. These members analyze the movement of the spinal vertebrae relative to each other. The results of this spinal movement analysis are used by a surgeon to help select the best therapy. Optimal therapy selection that is informed by objective information concerning spinal motion (including segmental relative mobility) can improve clinical effectiveness, as well as avoid the risk and expense of unnecessary spinal procedures and hardware.

As one example of how this device may be applied, a surgeon may have to decide whether or not to implant stabilization hardware to provide stabilization to support spinal fusion. If the objective analysis of spinal motion provided by this device indicates that the vertebrae are sufficiently stable on their own, then stabilization hardware may not need to be implanted. As another example, a surgeon may have to decide whether or not to replace a natural intervertebral disc, which may have become dysfunctional, with an artificial intervertebral disc. If the objective analysis of information provided by this device indicates that the natural intervertebral disc is doing a good job of resisting compression, then an artificial intervertebral disc may not need to be implanted. As another example, if the results of this device indicate asymmetry in spinal range of motion, then asymmetric dynamic stabilization of the spine may be appropriate.

This novel invention can provide surgeons with minimally-invasive, precise, and objective measurements concerning each of the multiple dimensions of spinal motion. It can independently isolate and measure spinal flexion, extension, lateral bending, decompression, compression, and torsion. The prior art does not provide surgeons with such information. Currently, surgeons have to rely on subjective assessments of spinal motion and the best devices in the prior art do not offer independent control of each dimension of movement. As a result, currently there is tremendous variation concerning which therapies are done for what conditions. It is very unlikely that quality is being optimized and costs are being best managed with such high variation in practice patterns. This variation may be greatly reduced by the availability of objective information concerning spinal motion. The objective measurements concerning each dimension of spinal movement that are provided by this device may be compared to normative measurements in order to determine the optimal therapy for each patient. Also, pre-decompression measurements may be compared to post-decompression measurements. In this manner, this device can provide objective and standardized evidence for these comparisons, guide therapy, improve the quality of care for each patient, and avoid the costs and risks of unnecessary spinal procedures and hardware.

INTRODUCTION TO THE FIGURES

These figures show one possible embodiment of this invention, but do not limit the full generalizability of the claims.

DETAILED DESCRIPTION OF THE FIGURES

These figures show one possible embodiment of this invention. However, this invention may also be embodied in other ways. These figures do not limit the full generalizability of the claims.

Figure 1:
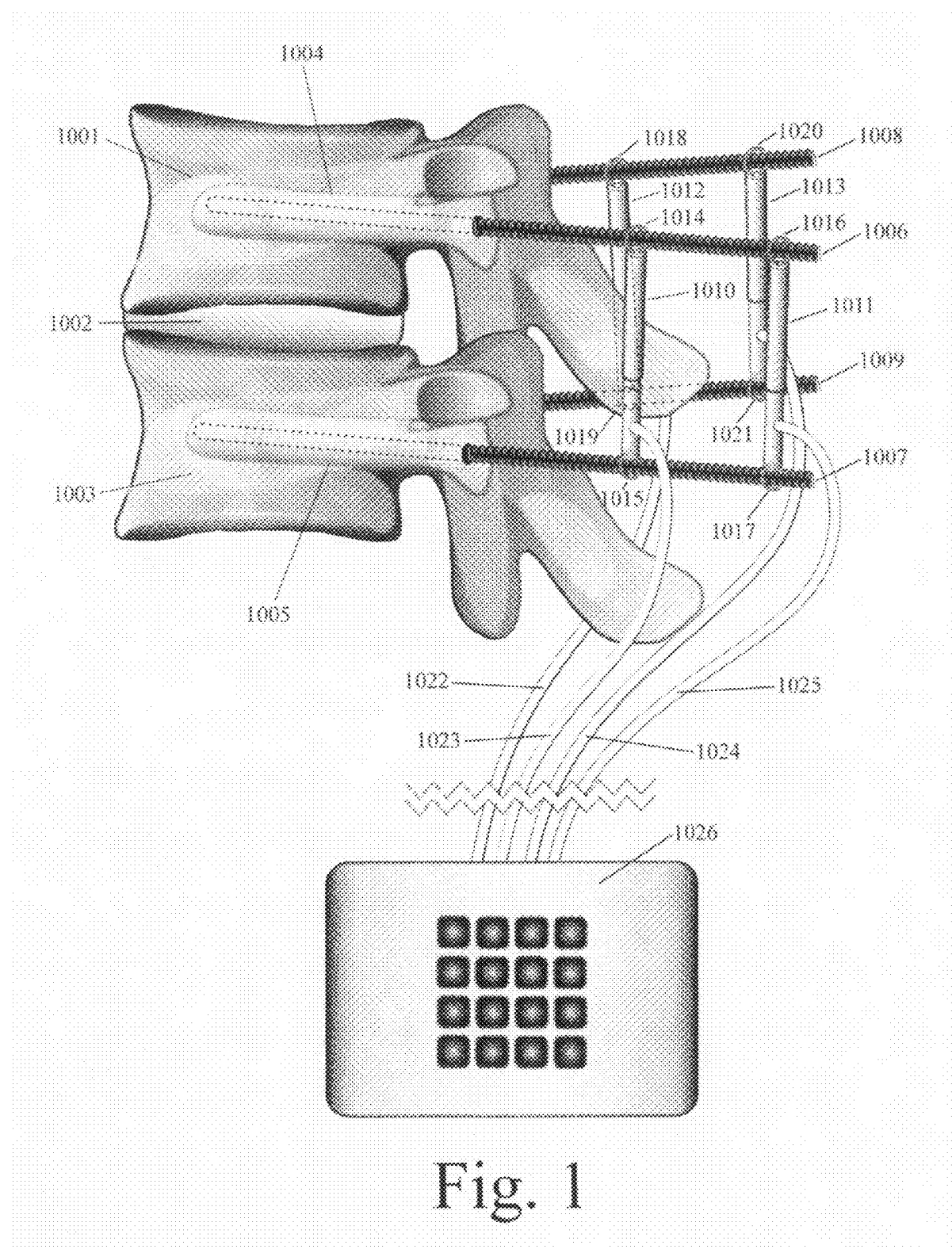
FIG. 1 shows an embodiment of this device with four rods inserted into two spinal vertebrae wherein these rods are connected by hydraulic members that move the rods that, in turn, move the vertebrae.

FIG. 1 shows one embodiment of this device that is used to both cause and measure the movement of spinal vertebrae in order to provide a surgeon with objective information to help the surgeon select the optimal therapy for a patient. This particular embodiment has four rods that are inserted into the spinal vertebrae. In this example, these rods are threaded to enable tapping into pedicles in a manner analogous to the manner used for pedicle screws. This embodiment also has adjustable-length hydraulic members which are attached to these rods. The hydraulic members move the rods that, in turn, move the vertebrae. This embodiment also measures the movement of the vertebrae. A control unit analyzes the relationship between the forces that are applied to the vertebrae through the rods and the manner in which the vertebrae are moved by these forces. Analysis of this relationship can help to guide the selection of a therapeutic option from among therapeutic options such as exercise, dynamic stabilization of the spine, and complete spinal fusion.

In particular, the embodiment shown in FIG. 1 is applied to two spinal vertebrae, 1001 and 1003, with an intervertebral disc, 1002, between these spinal vertebrae. This embodiment has four threaded rods 1006, 1007, 1008, and 1009 that have been partially inserted into the pedicles 1004 and 1005 of spinal vertebrae 1001 and 1003 such that the proximal ends of these rods protrude from the pedicles.

In this example, these rods have been inserted into the body in a minimally-invasive percutaneous manner with x-ray assistance through small openings in the tissue of the patient's back. In this example, the proximal ends of these rods protrude out from the skin of the back, allowing minimally-invasive application of forces to the vertebrae by applying forces to the rods. Application of these forces can change the relative movement and positions of the vertebrae. In this example, insertion of these rods was done through the insertion and removal of a sequence of longitudinal members with progressively-larger diameters to bore holes with progressively-larger diameters in the pedicles, culminating in the insertion of the rods. In this example, the insertion of these longitudinal members, including the rods, was guided from the surface tissue into the pedicles via x-ray imaging. In other examples, other types of medical imaging may be used to guide insertion of rods and longitudinal members. Insertion of the longitudinal members may be done manually or by automated means. In other examples, the rods may be inserted into surgically-exposed vertebrae.

In the example shown in FIG. 1, the four rods, 1006, 1007, 1008, and 1009, that have been inserted into the vertebrae are connected by four adjustable-length, parallel, hydraulic members 1010, 1011, 1012 and 1013. In this example, these adjustable-length hydraulic members are attached to the rods by fasteners 1014, 1015, 1016, 1017, 1018, 1019, and 1020, 1021. In this example, these adjustable-length members are hydraulic members, comprised of concentric cylindrical members filled with a liquid. Their lengths can be adjusted by changing the pressure and volume of the liquid inside them. In another example, these adjustable-length members may be pneumatic members whose lengths may be changed by changing the pressure and volume of a gas inside them. In another example, these adjustable-length members may be threaded rods that are inserted into a concentric threaded connector, wherein rotation of either the rod or the connector changes their length. This rotation may be done by an electric motor. In another example, members inserted into the vertebrae, such as rods, may be directly manipulated by human force rather than by hydraulic, pneumatic, or electric motor means. In various examples, movement of bone moving members may be caused by a means selected from the group consisting of: electric motor; hydraulic pressure; pneumatic pressure; vacuum; rotation of a threaded member; and manually-performed human force.

In this example, there are two parallel adjustable-length hydraulic members 1010 and 1011 that connect rods 1006 and 1007 which, in turn, connect pedicles 1004 and 1005 on the near side of vertebrae 1001 and 1003. Similarly, there are two parallel adjustable-length hydraulic members 1012 and 1013 that connect rods 1008 and 1009 which, in turn, connect the pedicles on the far side of vertebrae 1001 and 1003. In other examples, there may be more than two parallel adjustable-length members connecting each pair of rods. In other examples, there may be non-parallel adjustable-length members that connect pairs of rods. In other examples, there may be other methods of moving longitudinal members inserted into vertebrae other than adjustable-length members. For example, longitudinal members inserted into vertebrae may be moved by adjusting the tensions of tensile members that connect them.

The different movements of the spine are generally classified into flexion, extension, lateral bending, decompression, compression, and torsion. These movements may be informally defined as follows. Spinal flexion may be informally defined as the spine "bending forward." Spinal extension may be informally defined as the spine "bending backwards." Spinal lateral bending may be informally defined as the spine "bending to the right or left." Spinal decompression may be informally defined as "vertical elongation" of the spine. Spinal compression may be informally defined as "vertical shortening" of the spine. Spinal torsion may be informally defined as "vertical twisting" of the spine.

Although these movement definitions are adequate for many purposes, they are insufficiently precise for carefully evaluating the prior art in this area and for highlighting the novel advantages of this present invention. These informal definitions are not sufficiently precise for isolating these movements from each other. This present invention allows isolation and independent control over each of these individual movements in a precise manner that is not possible with devices in the prior art. The individual movements are either confounded, or not measureable at all, by devices in the prior art. For these reasons, we now present more formal and precise definitions of spinal flexion, extension, lateral bending, decompression, compression, and torsion.

Spinal flexion may be formally defined as spinal movement that changes a linear angle formed by the intersection of the lateral cross-sectional planes of two vertebrae, wherein the vertex of this angle is anterior to the center of the vertebrae. The amount of flexion is the degree of the linear angle formed by the intersection of the lateral cross-sectional planes of two vertebrae, wherein the vertex of this angle is anterior to the center of the vertebrae. Simple application of one or more forces to a single point on each of the vertebrae (either directly to the vertebrae or to members inserted into the vertebrae) as in the prior art does not provide sufficient control to adjust and measure flexion independently from decompression and compression. In contrast, application of force to multiple points on longitudinal members inserted into vertebrae, as shown in this embodiment of this invention, can adjust and measure flexion independently from decompression and compression.

Spinal extension may be formally defined as spinal movement that changes a linear angle formed by the intersection of the lateral cross-sectional planes of two vertebrae, wherein the vertex of this angle is posterior to the center of the vertebrae. The amount of extension is the degree of the linear angle formed by the intersection of the lateral cross-sectional planes of two vertebrae, wherein the vertex of this angle is posterior to the center of the vertebrae. Simple application of one or more forces to a single point on each of the vertebrae (either directly to the vertebrae or to members inserted into the vertebrae) as in the prior art does not provide sufficient control to adjust and measure extension independently from decompression and compression. In contrast, application of force to multiple points on longitudinal members inserted into vertebrae, as shown in this embodiment of this invention, can adjust and measure extension independently from decompression and compression.

Spinal lateral bending may be formally defined as spinal movement that changes a linear angle formed by the intersection of the lateral cross-sectional planes of two vertebrae, wherein the vertex of this angle is to the right or left of the center of the vertebrae. The amount of lateral bending is the degree of the linear angle formed by the intersection of the lateral cross-sectional planes of two vertebrae, wherein the vertex of this angle is to the right or left of the center of the vertebrae. Simple application of one or more forces to a single point on each of the vertebrae (either directly to the vertebrae or to members inserted into the vertebrae) as in the prior art does not provide sufficient control to adjust and measure lateral bending independently from decompression and compression. In contrast, application of force to multiple points on longitudinal members inserted into vertebrae, as shown in this embodiment of this invention, can adjust and measure lateral bending independently from decompression and compression.

Spinal decompression may be formally defined as spinal movement that increases the average distance between all points in the lateral cross-sections of two spinal vertebrae. Simple application of one or more forces to a single point on each of the vertebrae (either directly to the vertebrae or to members inserted into the vertebrae) in prior art does not provide sufficient control to adjust and measure decompression independently from flexion, extension, and/or lateral bending. In contrast, application of force to multiple points on longitudinal members inserted into the vertebrae, as shown in this embodiment of this invention, can adjust and measure decompression independently from flexion, extension, and lateral bending.

Spinal compression may be formally defined as spinal movement that decreases the average distance between all points in the lateral cross-sections of two spinal vertebrae. Simple application of one or more forces to a single point on each of the vertebrae (either directly to the vertebrae or to members inserted into the vertebrae) in prior art does not provide sufficient control to adjust and measure compression independently from flexion, extension, and/or lateral bending. In contrast, application of force to multiple points on longitudinal members inserted into vertebrae, as shown in this embodiment of this invention, can adjust and measure compression independently from flexion, extension, and lateral bending.

Spinal torsion may be formally defined as spinal movement that rotates the lateral cross-sectional plane of one vertebra around the vertical axis of the vertebra relative to the cross-sectional plane of a second vertebra. Application of forces to points that are vertically aligned on vertebrae in the prior art does not allow independent adjustment and measurement of torsion. In contrast, application of force to multiple points on longitudinal members, or to members that are not vertically aligned, can adjust and measure torsion.

This embodiment of this invention features two longitudinally-separated locations along the longitudinal axis of each rod, with the ability to independently adjust the forces applied to each of these locations. This allows full control over the angle formed by the intersection of these longitudinal axes. If these longitudinal axes do not share a common plane in three dimensional space, then this statement can apply to the angle formed by the projection of these longitudinal axes onto a common plane. This degree of angle control is not possible with devices in the prior art that apply force to only one point on each vertebrae or to only one point on each member that is inserted into a vertebrae. The full movement control provided by this invention can cause movement of spinal vertebrae relative to each other: wherein this movement is selected from the group consisting of flexion, extension, lateral bending, decompression, compression, and torsion; and wherein these bone moving members provide the ability to cause each of these movements independently, without confounding one or more other movements in this group. Devices in the prior art do not offer this capability.

In an example, movement of the bone moving members (rods in this embodiment) can cause spinal vertebrae to move in flexion, extension, or lateral bending. In an example, movement of the bone moving members (rods in this embodiment) can cause spinal vertebrae to move in decompression or compression. In an example, movement of the bone moving members (rods in this embodiment) can cause spinal vertebrae to move in torsion. In an example, this device can allow movement to be selected from any of the movements in the group consisting of flexion, extension, lateral bending, decompression, compression, and torsion—wherein the amount of each type of movement can be independently controlled.

In an example, movement of the spinal vertebrae can be caused by movement of members (rods in this embodiment) that are inserted into one or more vertebrae. In another example, movement of the spinal vertebrae can be caused by movement of one or more members that are adhered to the surface of one or more vertebrae. In another example, movement of the spinal vertebrae can be caused by movement of one or more members that are compressively or elastically attached to the surface of one or more vertebrae. In yet another example, movement of the spinal vertebrae can be caused by movement of one or more members that are not attached to, but rather press against, the surfaces of one or more vertebrae.

We now move on from discussion of spinal flexion, extension, lateral bending, decompression, compression, and torsion to discuss the remaining components in FIG. 1. FIG. 1 also shows tubes 1022, 1023, 1024 and 1025 connecting adjustable-length members 1010, 1011, 1012, and 1013 with control unit 1026. In this example wherein adjustable-length members 1010, 1011, 1012, and 1013 are hydraulic members, tubes 1022, 1023, 1024 and 1025 contain pressurized liquid.

In this example, control unit 1026 is used to adjust the pressure and volume of liquid within each of the adjustable-length members. Changes in the fluid pressure within each adjustable-length member changes the amount of force that this member exerts between the insertable rods to which the adjustable-length hydraulic member is connected. This change in force changes, in turn, the force acting on the vertebrae to which the insertable rods are connected. The changes in force on the vertebrae, in turn, cause the vertebrae to move in flexion, extension, lateral bending, decompression, compression, torsion, or a combination thereof.

In this example, not only do the adjustable-length hydraulic members cause movement of the spinal vertebrae, but these hydraulic members are also used to measure this movement. In an example, changes in the volume of the liquid entering or exiting an adjustable-length hydraulic member can be used to estimate changes in the length of that member. Further, information concerning the lengths of all of the adjustable-length hydraulic members can be analyzed to infer the movement of the spinal vertebrae relative to each other.

The overall pattern of changes in the lengths of all four of the adjustable-length members can be used to measure the flexion, extension, lateral bending, decompression, compression, and/or torsion of the spinal vertebrae.

In this example, the same members (adjustable-length hydraulic members in this example) are used to both cause and measure movement of the spinal vertebrae. In another example, separate members may be used to perform the movement-causation function and the movement-measurement function. For example, movement may be caused by hydraulic, pneumatic, threaded, or tensile members and movement may be measured by electrogoniometers.

In this example, information concerning movement of spinal vertebrae due to the forces applied to them is collected and analyzed within control unit 1026. There are many examples of information analysis algorithms in the prior art and their precise specification is not central to this invention, so they are not detailed herein. This information is analyzed in order to help select a particular therapy. For example, a surgeon may have to decide whether to implant stabilization hardware to provide stabilization for a spinal fusion. If analysis of information from this device indicates that the vertebrae are sufficiently stable on their own, then stabilization hardware may not be needed. As another example, a surgeon may have to decide whether to replace the natural intervertebral disc with an artificial intervertebral disc. In another example, the surgeon may decide whether to perform some type of intervertebral fusion procedure to increase disk space height and prevent neuroforminal compression. If analysis of information from this device indicates that the natural disc does a good job resisting decompression, then an artificial intervertebral disc may be unnecessary. As another example, if the results of this device indicate asymmetric range of motion, then asymmetric dynamic stabilization of the spine may be appropriate.

In these ways, this invention can provide surgeons with a minimally-invasive, precise method to create and objectively analyze pure flexion, pure extension, pure lateral bending, pure decompression, pure compression, and pure torsion in order to determine the optimal therapy for a particular patient. This provides objective data and criteria for therapy selection that can improve the quality of care and avoid the risks and costs of unnecessary revision procedures and hardware.

Figure 2:
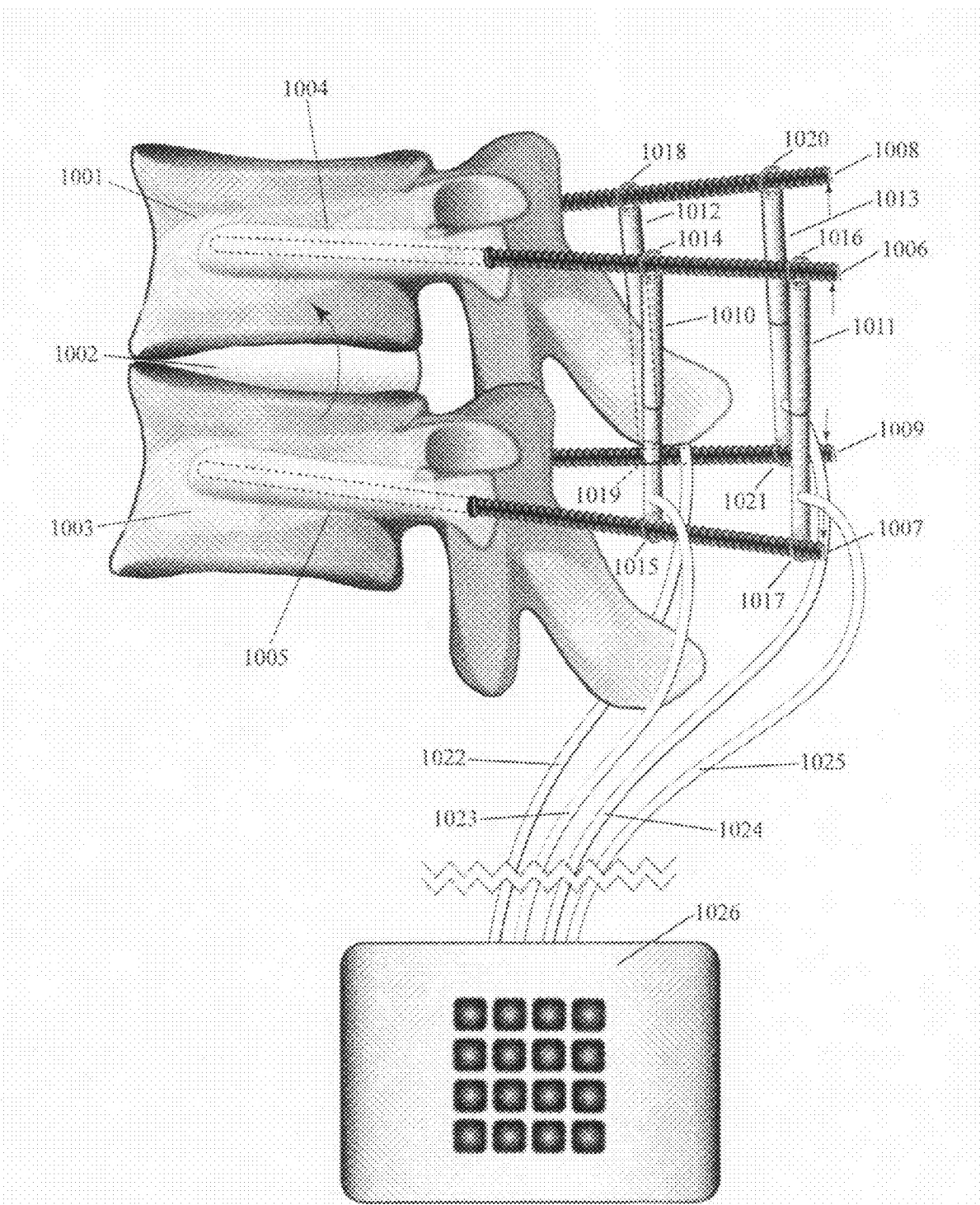
FIG. 2 shows this same embodiment, except that the four rods have been moved to cause flexion of the spinal vertebrae.

FIG. 2 shows the same embodiment of this invention that was shown in FIG. 1, except that now the four rods 1006, 1007, 1008, and 1009 have been moved to cause flexion of the spinal vertebrae. In FIG. 2, all four adjustable-length hydraulic members 1010, 1011, 1012 and 1013 have been lengthened. However, hydraulic members 1011 and 1013 have been lengthened by an equal amount that is greater than the amount by which hydraulic members 1010 and 1012 have been lengthened. This pattern of selective elongation pushes the ends of rods 1006 and 1008 upwards by equal amounts, tilting vertebra 1001 counter-clockwise, and pushes the ends of rods 1007 and 1009 downwards by equal amounts, tilting vertebra 1003 clockwise. The result is spinal flexion.

The ability of this embodiment of this invention to independently adjust the lengths of these hydraulic members along different places on the longitudinal axes of the rods allows adjustment of flexion independently of decompression or compression. This is an advantage over the prior art that confounds flexion with decompression. Control unit 1026 analyzes the relationship between the forces applied to the vertebrae by the hydraulic members and the resulting flexion of the vertebrae (as estimated by measuring changes in the volume of fluid entering or exiting the hydraulic members). This analysis is then used by a surgeon to guide the choice of therapy.

Figure 3:
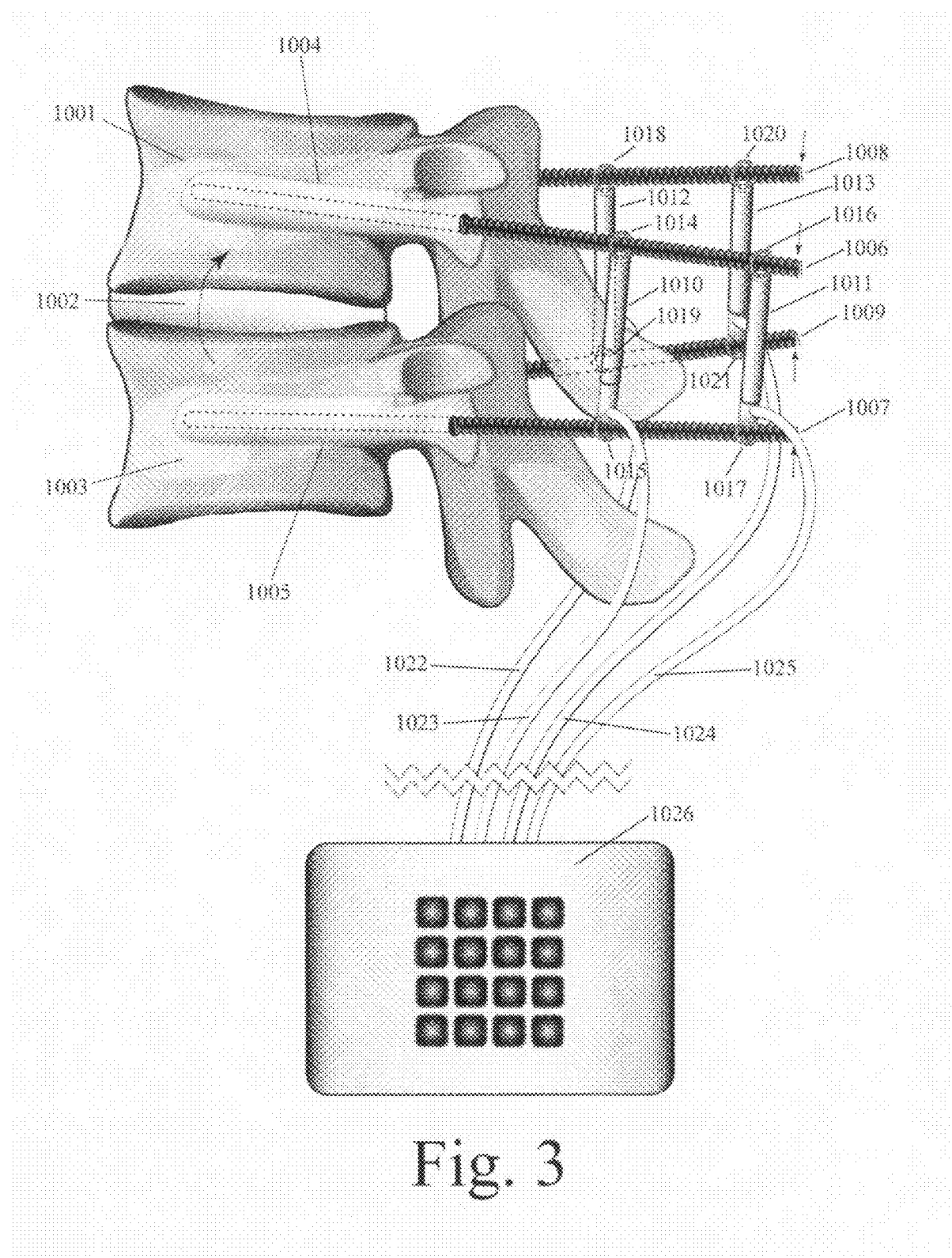
FIG. 3 shows this same embodiment, except that the four rods have been moved to cause extension of the spinal vertebrae.

FIG. 3 also shows the same embodiment of this invention that was shown in FIG. 1, except that now the four rods 1006, 1007, 1008, and 1009 have been moved to cause extension of the spinal vertebrae. In FIG. 3, all four adjustable-length hydraulic members 1010, 1011, 1012 and 1013 have been shortened. However, hydraulic members 1011 and 1013 have been shortened by an equal amount that is greater than the amount by which hydraulic members 1010 and 1012 have been shortened. This pattern of selective shortening pulls the ends of rods 1006 and 1008 downwards by equal amounts, tilting vertebra 1001 clockwise, and pulls the ends of rods 1007 and 1009 upwards by equal amounts, tilting vertebra 1003 counter-clockwise. The result is spinal extension.

The ability of this embodiment of this invention to independently adjust the lengths of these hydraulic members along different places on the longitudinal axes of the rods allows adjustment of extension independently of decompression or compression. This is an advantage over the prior art that confounds extension with compression. Control unit 1026 analyzes the relationship between the forces applied to the vertebrae by the hydraulic members and the resulting extension of the vertebrae (as estimated by measuring changes in the volume of fluid entering or exiting the hydraulic members). This analysis is then used by a surgeon to guide the choice of therapy.

Figure 4:
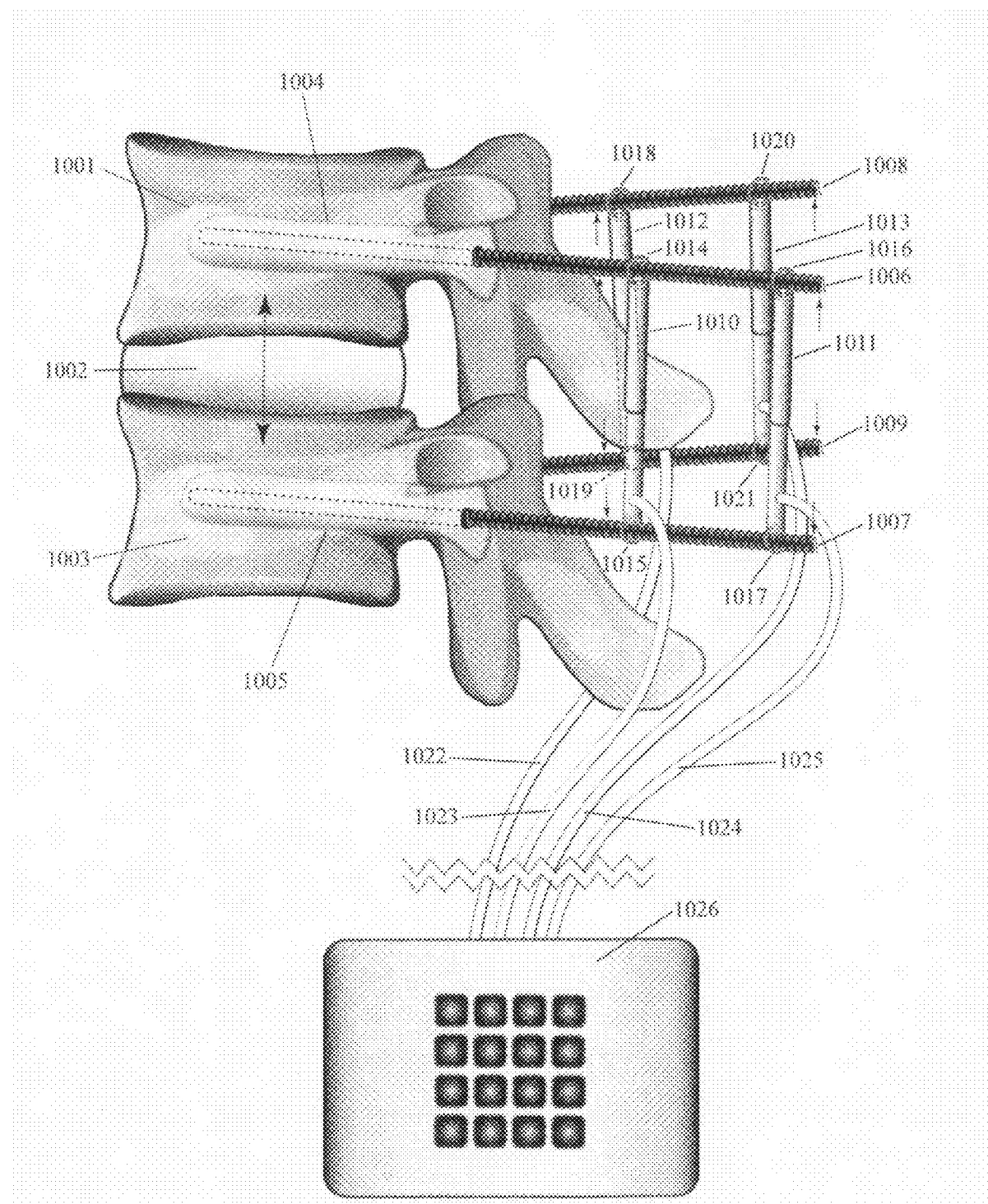
FIG. 4 shows the same embodiment, except that the four rods have been moved to cause decompression of the spinal vertebrae.

FIG. 4 also shows the same embodiment of this invention that was shown in FIG. 1, except that now the four rods 1006, 1007, 1008, and 1009 have been moved to cause decompression of the spinal vertebrae. In FIG. 4, all four adjustable-length hydraulic members 1010, 1011, 1012 and 1013 have all been lengthened by an equal amount. This pattern of uniform lengthening pushes rods 1006 and 1008 upwards in parallel and pushes rods 1007 and 1009 downwards in parallel. Unlike pushing or pulling primarily on the ends of the rods, as was done in FIGS. 2 and 3, pushing rods in parallel as in FIG. 4 does not tilt the vertebrae. These parallel pushing or pulling actions result in pure decompression or pure compression of the vertebrae. FIG. 4, in particular, shows pure decompression.

The ability of this embodiment of this invention to independently adjust the lengths of these hydraulic members along different places on the longitudinal axes of the rods allows adjustment of decompression or compression independently of flexion, extension, or lateral bending. This is an advantage over the prior art that confounds decompression with flexion. Control unit 1026 analyzes the relationship between the forces applied to the vertebrae by the hydraulic members and the resulting decompression of the vertebrae (as estimated by measuring changes in the volume of fluid entering or exiting the hydraulic members). This analysis is then used by a surgeon to guide the choice of therapy.

Figure 5:
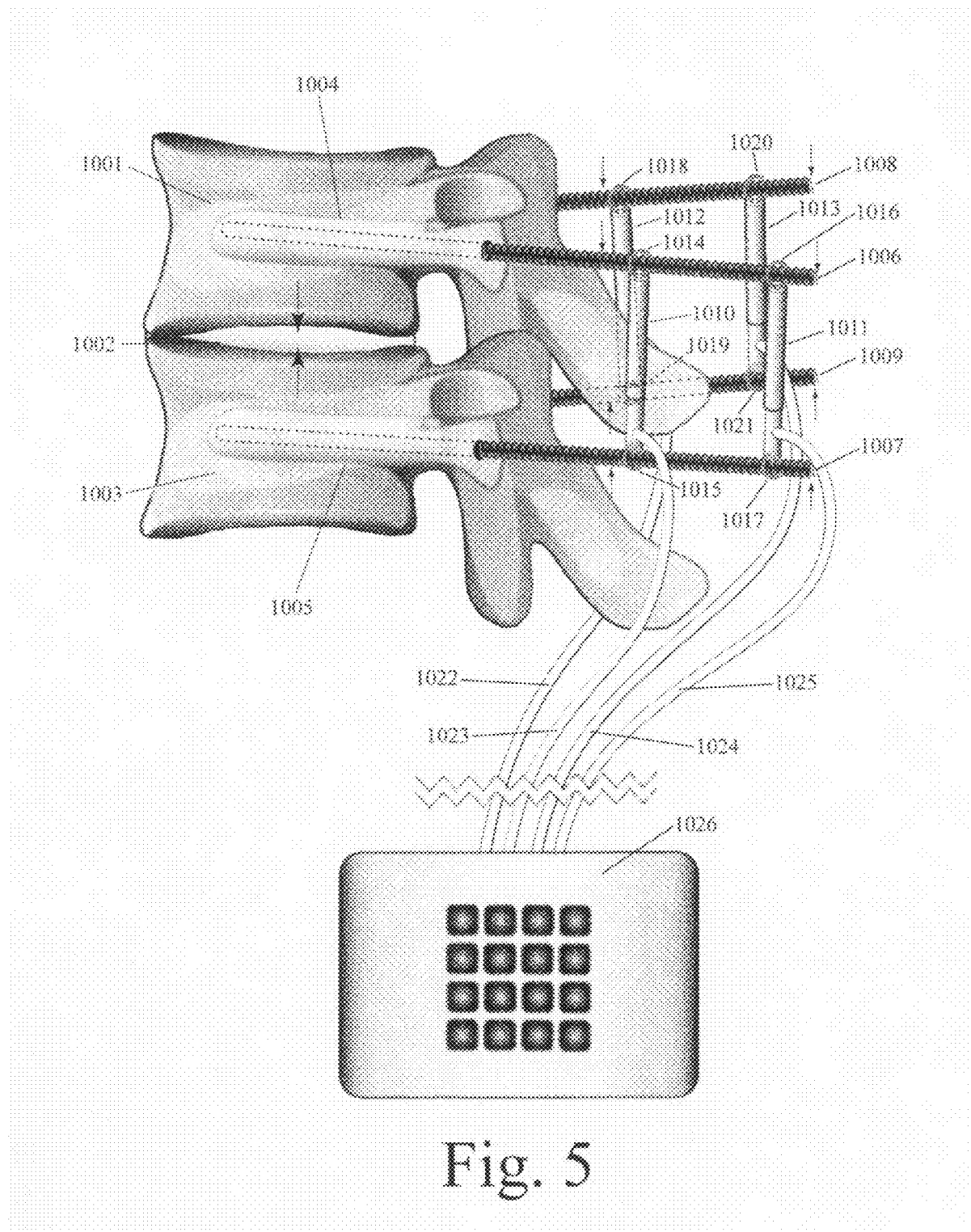
FIG. 5 shows the same embodiment, except that the four rods have been moved to cause compression of the spinal vertebrae.

FIG. 5 also shows the same embodiment of this invention that was shown in FIG. 1, except that now the four rods 1006, 1007, 1008, and 1009 have been moved to cause compression of the spinal vertebrae. In FIG. 5, all four adjustable-length hydraulic members 1010, 1011, 1012 and 1013 have all been shortened by equal amounts. This pattern of uniform shortening pulls rods 1006 and 1008 downwards in parallel and pulls rods 1007 and 1009 upwards in parallel. Pulling rods in parallel, as done here, does not tilt the vertebrae. These actions result in pure compression.

The ability of this embodiment of this invention to independently adjust the lengths of these hydraulic members along different places on the longitudinal axes of the rods allows adjustment of compression independently of flexion, extension, or lateral bending. This is an advantage over the prior art that confounds compression with extension. Control unit 1026 analyzes the relationship between the forces applied to the vertebrae by the hydraulic members and the resulting compression of the vertebrae (as estimated by measuring changes in the volume of fluid entering or exiting the hydraulic members). This analysis is then used by a surgeon to guide the choice of therapy.

Figure 6:
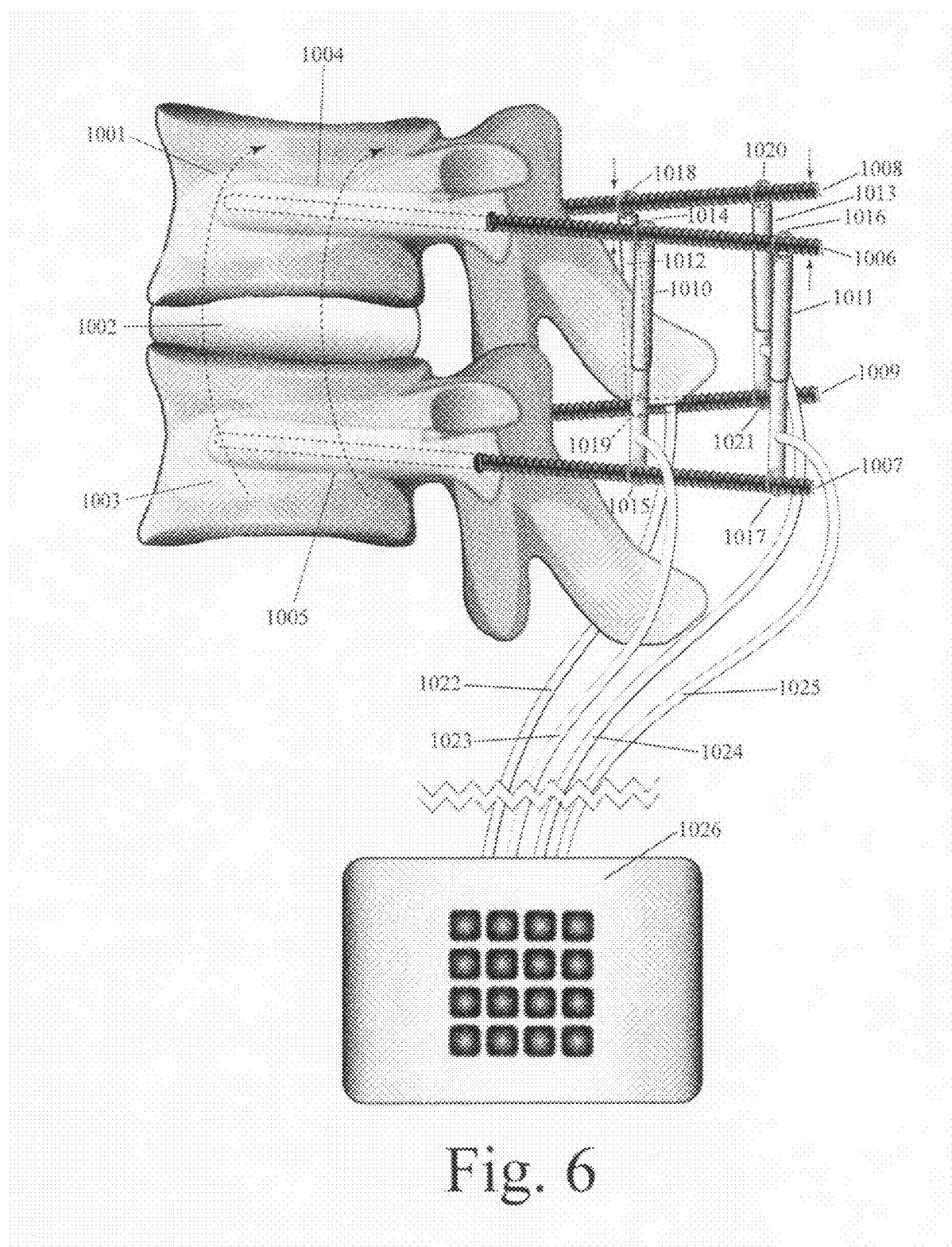
FIG. 6 shows the same embodiment, except that the four rods have been moved to cause lateral bending of the spinal vertebrae.

FIG. 6 also shows the same embodiment of this invention that was shown in FIG. 1, except that now the four rods 1006, 1007, 1008, and 1009 have been moved to cause lateral bending of the spinal vertebrae. In FIG. 6, hydraulic members 1010 and 1011 have been lengthened by an equal amount and hydraulic members 1012 and 1013 have been shortened by an equal amount. This pattern of lengthening and shortening pushes rod 1006 upwards (and possibly rod 1007 downwards) and pulls rod 1008 downwards (and possibly rod 1009 upwards). This pattern of pushing and pulling laterally tilts (laterally bends) the vertebrae relative to each other.

The ability of this embodiment of this invention to independently adjust the lengths of these hydraulic members along different places on the longitudinal axes of the rods allows adjustment of lateral bending independently of decompression or compression. This is an advantage over the prior art that confounds lateral bending with decompression or compression. Control unit 1026 analyzes the relationship between the forces applied to the vertebrae by the hydraulic members and the resulting lateral bending of the vertebrae (as estimated by measuring changes in the volume of fluid entering or exiting the hydraulic members). This analysis is then used by a surgeon to guide the choice of therapy.

Figure 7:
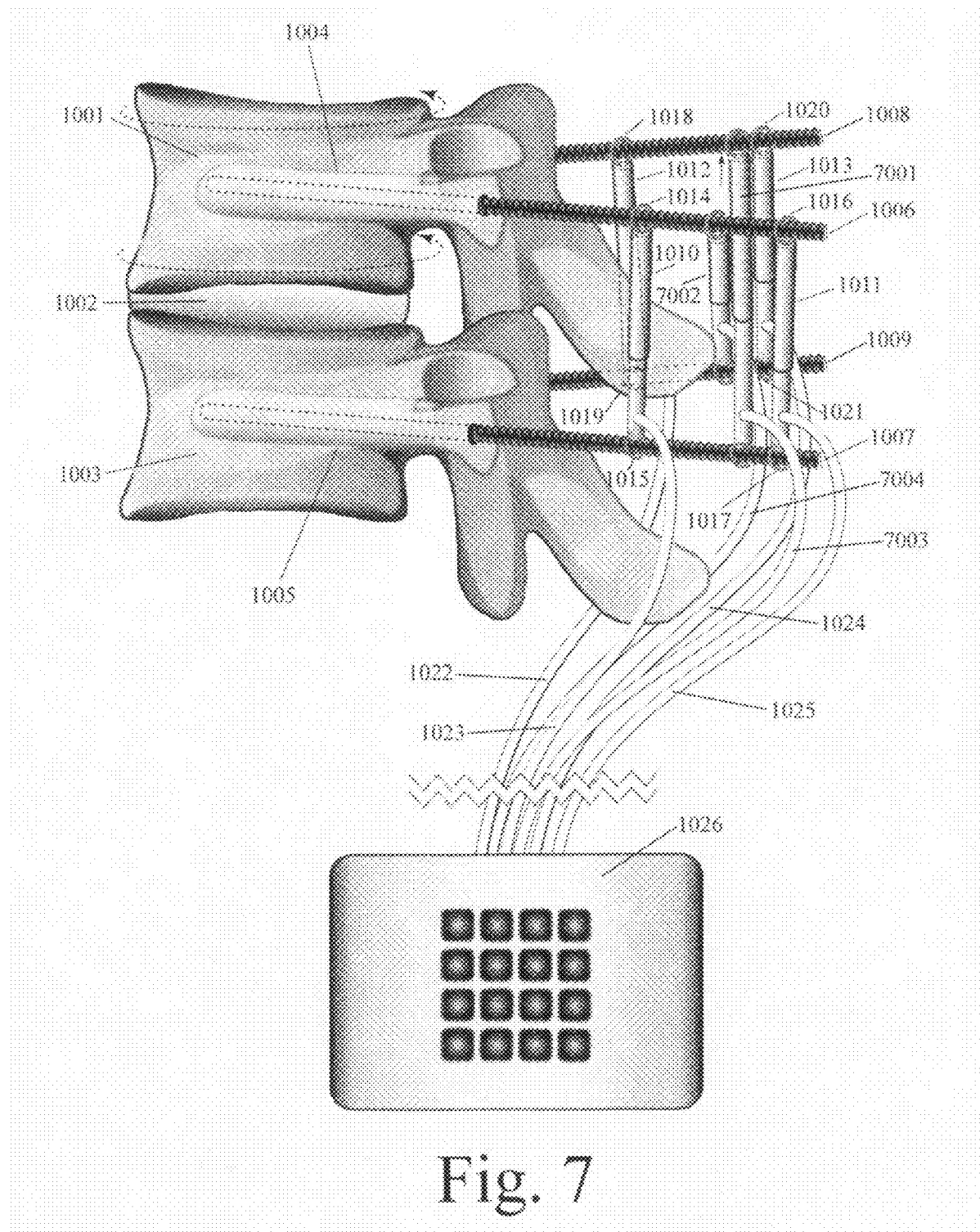
FIG. 7 shows the same embodiment, except that two added hydraulic members now exert torque on the vertebrae, causing them to move in torsion.

FIG. 7 shows the same embodiment of this invention that was shown in FIG. 1, except that two additional adjustable-length hydraulic members, 7001 and 7002, have been added. Hydraulic member 7001 transversely connects rod 1007 to rod 1008. Hydraulic member 7002 transversely connects rod 1006 to rod 1009. Due to the transverse nature of these connections, when the length of one of these transverse hydraulic members is changed, this exerts torque on the vertebrae, causing them to move in torsion.

In this example, hydraulic member 7001 has been lengthened, pushing rod 1008 away from diagonally-opposite rod 1007, thereby exerting torque on the vertebrae. As a result, vertebra 1001 rotates around its vertical axis relative to vertebra 1003. This is torsion. Such ability to create and measure torsion is an advantage over the prior art. Control unit 1026 analyzes the relationship between the forces applied to the vertebrae by the hydraulic members and the resulting torsion of the vertebrae (as estimated by measuring changes in the volume of fluid entering or exiting the hydraulic members). This analysis is then used by a surgeon to guide the choice of therapy.

We claim:

1. A first bone-moving member which has a longitudinal axis, wherein the distal portion of this longitudinal axis is configured to be inserted into a first spinal vertebra, wherein the proximal portion of this longitudinal axis is configured to protrude out from the skin of a person's back, one or more actuators to apply force to at least two longitudinally-separated locations along the proximal portion of the longitudinal axis of this bone-moving member; and wherein this application of force is active and not just passive resistance of force that comes from natural muscle movement; wherein the one or more actuators are electric, hydraulic or pneumatic actuators; a second bone-moving member which has a longitudinal axis, wherein the distal portion of this longitudinal axis is configured to be inserted into a second spinal vertebra, wherein the proximal portion of this longitudinal axis is configured to protrude out from the skin of a person's back, wherein the one or more actuators apply force to at least two longitudinally-separated locations along the proximal portion of the longitudinal axis of this bone-moving member; wherein this application of force is active and not just passive resistance of force that comes from natural muscle movement; wherein movement of a least one of the first and second bone-moving members causes vertebral movement of the first and second spinal vertebrae relative to each other; wherein this vertebral movement is selected from one, or a combination, of the movements in the group consisting of flexion, extension, lateral bending, decompression, compression, and torsion; wherein an amount of flexion or extension can be adjusted independently of an amount of decompression or compression; and wherein an amount of decompression or compression can be adjusted independently of an amount of flexion or extension; one or more bone movement measuring members that measure movement of the first and second spinal vertebrae relative to each other in response to the active application of force to the first and/or second bone-moving members; and one or more movement analyzing members that analyze movement of the first and second spinal vertebrae relative to each other, wherein the results of this analysis are used to help select a therapy.

2. The device in claim 1 wherein amounts of flexion, extension, or lateral bending are defined as follows: an amount of flexion is the degree of a linear angle formed by the intersection of the lateral cross-sectional planes of two vertebrae, wherein the vertex of this angle is anterior to the center of the vertebrae; an amount of extension is the degree of a linear angle formed by the intersection of the lateral cross-sectional planes of two vertebrae, wherein the vertex of this angle is posterior to the center of the vertebrae; and an amount of lateral bending is the degree of a linear angle formed by the intersection of the lateral cross-sectional planes of two vertebrae, wherein the vertex of this angle is to the right or left of the center of the vertebrae.

3. The device in claim 1 wherein amounts of decompression or compression are defined as follows: decompression is movement that increases the average distance between all points in the lateral cross-sections of two vertebrae; and compression is movement that decreases the average distance between all points in the lateral cross-sections of two vertebrae.

4. The device in claim 1 wherein analysis of flexion, extension, lateral bending, decompression, compression, and/or torsion is used to determine the extent to which vertebrae should be stabilized by application of stabilization procedures and/or devices.

5. A first bone-moving member which has a longitudinal axis, wherein the distal portion of this longitudinal axis is configured to be inserted into a first spinal vertebra, wherein the proximal portion of this longitudinal axis is configured to protrude out from the skin of a person's back, one or more actuators to apply force to at least two longitudinally-separated locations along the proximal portion of the longitudinal axis of this bone-moving member; and wherein this application of force is active and not just passive resistance of force that comes from natural muscle movement; wherein the one or more actuators are electric, hydraulic or pneumatic actuators; a second bone-moving member which has a longitudinal axis, wherein the distal portion of this longitudinal axis is configured to be inserted into a second spinal vertebra, wherein the proximal portion of this longitudinal axis is configured to protrude out from the skin of a person's back, wherein the one or more actuators apply force to at least two longitudinally-separated locations along the proximal portion of the longitudinal axis of this bone-moving member; wherein this application of force is active and not just passive resistance of force that comes from natural muscle movement; wherein movement of a least one of the first and second bone-moving members causes vertebral movement of the first and second spinal vertebrae relative to each other; wherein this vertebral movement is selected from one, or a combination, of the movements in the group consisting of flexion, extension, lateral bending, decompression, compression, and torsion; wherein an amount of flexion or extension can be adjusted independently of an amount of decompression or compression; and wherein an amount of decompression or compression can be adjusted independently of an amount of flexion or extension; one or more bone movement measuring members that measure movement of the first and second spinal vertebrae relative to each other in response to the active application of force to the first and/or second bone-moving members; and one or more movement analyzing members that analyze movement of the first and second spinal vertebrae relative to each other, wherein the results of this analysis are used to help select a therapy.

6. The device in claim 5 wherein the bone-moving members cause spinal vertebrae to move in flexion, extension, lateral bending, decompression, compression, or torsion.

7. The device in claim 5 wherein analysis of flexion, extension, lateral bending, decompression, compression, and/or torsion is used to determine the extent to which vertebrae should be stabilized by application of stabilization procedures and/or devices.

* * * * *